(12) United States Patent
Greb et al.

(10) Patent No.: US 7,455,856 B2
(45) Date of Patent: Nov. 25, 2008

(54) LIPID-DERIVATIZED BISPHOSPHONIC ACID

(75) Inventors: Wolfgang Greb, Düsseldorf (DE); Oleg Shyhskov, Bremen (DE); Gerd-Volker Röschenthaler, Bremen (DE); Verena Hengst, Düsseldorf (DE)

(73) Assignee: MCS Micro Carrier Systems GmbH, Neuss (DE)

( * ) Notice: Subject to any disclaimer, the term of this patent is extended or adjusted under 35 U.S.C. 154(b) by 104 days.

(21) Appl. No.: 10/597,059

(22) PCT Filed: Jan. 24, 2005

(86) PCT No.: PCT/DE2005/000095

§ 371 (c)(1),
(2), (4) Date: Jul. 10, 2006

(87) PCT Pub. No.: WO2005/070952

PCT Pub. Date: Aug. 4, 2005

(65) Prior Publication Data

US 2007/0154537 A1    Jul. 5, 2007

(30) Foreign Application Priority Data

Jan. 23, 2004   (DE) ................ 10 2004 003 781

(51) Int. Cl.
*A61K 9/127*  (2006.01)
(52) U.S. Cl. .............. 424/450; 435/458; 552/506; 554/76
(58) Field of Classification Search ............ 424/450; 435/458; 552/506; 554/76
See application file for complete search history.

(56) References Cited

U.S. PATENT DOCUMENTS 4,732,998 A * 3/1988 Binderup ............ 558/161
4,942,036 A   7/1990 Geho et al.
5,391,776 A * 2/1995 Ueno et al. ............ 552/507

FOREIGN PATENT DOCUMENTS

WO    97/39004    10/1997
WO    97/49711    12/1997

OTHER PUBLICATIONS

Page et al., Novel Synthesis of Bis(phosphonic acid)-Steroid Conjugates, J. Org. Chem., 66 (11), 3704-3708, 2001.*
Szajnman et al., Bisphosphonates derived from fatty acids are potent inhibitors of *Trypanosoma cruzi* farnesyl pyrophosphate synthase, Bioorganic & Medicinal Chemistry Letters, 13, 19, 2003, 3231-3235.*
Sergio H. Szajnman et al.; Bisphosphonates Derived from Fatty Acids are Potent Inhibitors of *Trypanosoma cruzi* Farnesyl Pyrophosphate Synthase; Bioorganic & Medicinal Chemistry Letters; 12 (2003) 3231-3235.

M.-T. Hsu et al. ; Inhibition of streptocccal growth, F-ATPase and pyrophosphatase by diphosphonates; Oral Microbiology and Immunology; 1995: 10: 47-53.
Stanley T. Hirozawa; Use of electrochemical noise in the study of corrosion inhibition of aluminium by gem-diphosphonates; Proceedings of the 8th European Symposium on Corrosion Inhibitors (8SEIC), Ann. Univ. Ferrara, N.S., Sez. V. Suppl N. 10, 1995.
M. Paladini, Inhibition of metal catalysis in oil oxidation; Chemical Abstracts Service XP002323678; 1991:447975.
Akio Onda et al.; Manufacture of long fibers from plants including treatment by alkaline substances and hydrogen peroxide; Chemical Abstracts Service XP002323679; 1996:620880.

* cited by examiner

*Primary Examiner*—Yvonne Eyler
*Assistant Examiner*—Chukwuma O Nwaonicha
(74) *Attorney, Agent, or Firm*—Gudrun E. Huckett

(57) ABSTRACT

A bisphosphonic acid of the general formula (I)

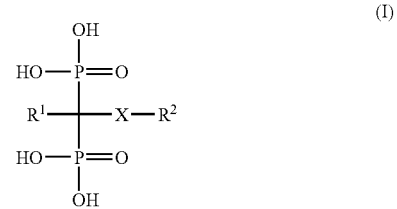

wherein $R^1$ is H, OH, $C_1$-$C_6$ alkyl $C_1$-$C_6$ alkoxy, $C_1$-$C_6$ hydroxyalkyl, $C_1$-$C_6$ aminoalkyl, $C_1$-$C_6$ halogen alkyl
X is a direct bond, alkylen group with 1 to 20 carbon atoms,
$(CH_3)_m$—$(OCR^3HCH_2)_n$—$(O)_o$—, wherein $R^3$ is H or $CH_3$ and m is 0 or a number from 1 to 6, n is a number from 1 to 10, preferably 1 to 6, and o is 0 or 1,
—$(CR^4HCH_2O)_p$—, wherein $R^4$ is H or $CH_3$, p is a number from 1 to 10, preferably 1 to 6,
$(CH_3)_q$—$(OCR^5HCH_2)_r$—$(O)_s$—$(CH_3)_t$—, wherein $R^5$ is H or $CH_3$ and q is 0 or a number from 1 to 6, r is a number from 1 to 10, preferably 1 to 6, and s is 0 or 1, and t is a number from 1 to 6,
$R^2$ is a group of the formula (II)

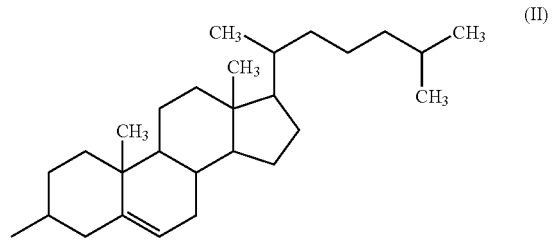

as well as their physiologically compatible derivatives in particular salts and trimethyl silyl derivatives.

13 Claims, No Drawings

LIPID-DERIVATIZED BISPHOSPHONIC ACID

BACKGROUND OF THE INVENTION

The present invention concerns cholesteryl-3-hydroxy-bisphosphonic acid derivatives and their soluble salts or hydrates and pharmacologically active conjugates, a method for their manufacture as well as their use for treating diseases.

Phosphonic Acid Derivatives and Their Technical Application

Phosphonic acids are organic components comprising one or several C—PO(OH)$_2$-group(s) with stable covalent carbon-phosphorus bonds. Phosphonates are effective chelating agents for divalent and trivalent metal ions. Most phosphonates are very similar to amino carboxylates such as EDTA, NTA, and DTPA. Moreover, they inhibit very effectively crystal growth and corrosion.

Based on these properties, they are used in numerous technical and industrial applications. An important field of application in industry is their use in cooling water, desalinating systems, and also on oil fields in order to inhibit corrosion. In the textile industry as well as in the paper and pulp production phosphonates are used as stabilizers for bleaching agents in that they act as chelating agents that can deactivated peroxide. An example for environmental use of phosphonates is glyphosate (N-phosphonomethyl glycine), a non-selective herbicide, that controls plant growth by inhibiting a biochemical cascade.

Polyphosphates represent polymers (condensation products) of orthophosphate groups that are bonded by energy-rich phosphoanhydride bonds (oxygen bonding). Polyphosphate (poly-P) is synthesized in the human body and is present almost in all cells. The largest proportion of poly-P can be found in the bone-forming osteoblasts. Poly-P has many functions, depending on which body section is being considered. It stores energy-rich phosphate, complexing calcium or other divalent or cations, it functions as a counter ion for basic amino acids or as a regulator of the intracellular level of adenylate nucleotides.

Poly-P is often used in toothpaste because it is assumed that it prevents caries formation which is assumed to be based on its ability to mineralize hydroxyl apatite and to reduce its acidity as well as its solubility.

The group of bisphosphonates is used for the treatment of different bone diseases and ailments that concern the calcium metabolism.

Bisphosphonates are analogues of pyrophosphate in which oxygen bonding is replaced by a carbon atom with different side chains. The P—C—P group is resistant in regard to enzymatic hydrolysis and for this reason bisphosphonates are not metabolized in the body. Bisphosphonates can be divided into three generations. They differ in regard to the substitution of the hydrogen atom by different side chains at two possible positions in the molecule. Alkyl side chains (for example, etidronate) characterize the first generation. The second generation of bisphosphonate comprises the amino bisphosphonate with a terminal amino group (for example, alendronate). Side chains that have rings are typical of the third generation (for example, zolendronate).

Medical Applications of Phosphonates

In bone scintigraphy phosphonates are used as diagnostic agents. Some differently marked phosphonates, for example, $^{99m}$TC-marked phosphonates or $^{188}$Re-complexes, are used as radioactive markers in order to make visible in the skeleton the presence, the location, and the degree of diseases, such as osteomyelitis, bone neoplasms, arthritis or bone infarcts.

The most important pharmacological effect of bisphosphonate is the inhibition of bone resorption. They have, like pyrophosphate, a high affinity to hydroxyl apatite, the main component of the bone, and prevent its growth as well as its decomposition. Moreover, they deactivate osteoclastic cells, called osteoclasts, in that they cause their apoptosis. Normally, the osteoclasts cooperate with bone-forming cells, the osteoblasts, in order to rebuild the existing bone. They target bone areas that have a high osteoclast activity and they contribute to the regeneration of the normal conditions between osteoblast activity and osteoclast activity.

Bisphosphonates are used in the therapy of bone diseases, usually in the case of Paget disease, hypercalcaemia, osteoporosis and neoplasms.

A further advantage of this group is that they can effect apoptosis of tumor cells. Therefore, they play an important role in cancer therapy (for example, in the case of breast cancer, metastases caused by prostate cancer, or in the case of multiple myeloma).

Derivatives that are comprised of acyclic nucleosidic phosphonates (for example, cidofovir or tenofovir) are effective against a large number of diseases caused by DNA viruses and retroviruses. Acyclic nucleosidic phosphonates (ANPs) are analogues in which one phosphonate is bonded by means of an aliphatic chain via an ether bond to a purine or a pyrimidine. As soon as these analogues are phosphorylized in the cell, they compete with naturally occurring nucleotides in nucleic acid synthesis; as a result of this, the virus replication in the infected cells is reduced or prevented.

The antiviral activity of ANPs is also utilized in veterinary medicine. They are potent inhibitors of the feline immunodeficiency virus (FIV). FIV is similar to the HI virus with regard to morphological, physical, and biochemical properties.

Homing Application for Effective Ingredients/Homing Ligands

As a result of the extraordinary affinity of bisphosphonates to hydroxyl apatite their suitability for homing applications in connection with pharmacologically active substances on the bone was examined. An example for this is the bonding of bisphosphonate, having a high affinity to bone, and growth factors (for example, bovin e serum albumin) that have the ability to stimulate bone growth. Radioisotopes, anti-neoplastic agents, and anti-inflammatory substances have also been bonded to these homing ligands.

The expression "active ingredient homing application" comprises substances that enable a time-controlled release, an organ-specific application, protection, extended in-vivo action, and reduction of toxicity of the active ingredients. Many carrier systems, for example, polymers, nanoparticles, microspheres, micelles, protein carrier systems, DNA complexes as well as liposomes have been used in order to extend the circulation time of different molecules in order to carry them to the desired location of action and in order to protect them from decomposition within the plasma. Liposomes have been utilized in the past as active ingredient carriers in various applications. They have colloidal, vesicular structures on the bases of (phosphor)-lipid bilayer membranes. Because of these structural properties they can encapsulate hydrophilic as well as hydrophobic molecules. Moreover, liposomes can be biologically decomposed and are essentially non-poisonous because they are comprised of natural biomolecules.

A limiting factor of liposomes as an active ingredient carrier is their decomposition by macrophages (copper cells) in the liver and in the spleen directly after intravenous application. The speed and the degree of their uptake are dependent on the rigidity of the membrane, the liposome size, and the dosage. A modification of the liposome surface can reduce the undesirable decomposition by macrophages. By bonding PEG units to the external membrane the circulation time can be increased significantly (long-circulating liposomes). Alternatively, homing molecules can be attached to the liposome bilayers in order to make these structures specific for the location of action, for example, immuno liposomes (liposomes that have at their surface covalently bonded antibodies as homing ligands); they can also be provided with long-circulating properties.

Passive Homing Application

Long-circulating liposomes have the tendency to accumulate in tissues that have a permeable endothelium. These "passive properties of the homing application" are very useful for the homing application on tumor tissues because the arrangement of the blood vessels of most tumors is sufficiently permeable for liposomes. Moreover, because the lymphatic tissue in tumors is usually not fully developed, the extrava sated liposomes have the tendency to remain within the interstitial spaces of the tumor tissue.

Long-circulating liposomes are used frequently as carriers for therapeutic cancer agents, for example, doxorubicin, cisplatinum, vincristine, and camphotecin.

Cholesterol

Cholesterol, when looking at its structure, is an important component of cell membranes. It has an effect on the physical properties of the membrane, especially its fluidity. It is used very frequently in the pharmaceutical industry, in particular, as a component of liposomes. Cholesterol has the property to make membranes more stiff. The addition of cholesterol transforms the membrane into an ordered fluid state across a wide temperature range. Moreover, the use of newly synthesized cholesterol derivatives has been studied already early on.

The afore described components have a plurality of positive properties in the treatment of the aforementioned diseases as well as in the administration of active ingredients.

SUMMARY OF THE INVENTION

The object of the present invention are bisphosphonic acids and derivatives thereof having the following formula (I)

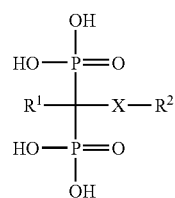

(I)

wherein $R^1$ is H, OH, $C_1$-$C_6$ alkyl $C_1$-$C_6$ alkoxy, $C_1$-$C_6$ hydroxyalkyl, $C_1$-$C_6$ aminoalkyl, $C_1$-$C_6$ halogen alkyl X is a direct bond, alkylen group with 1 to 20 carbon atoms, $(CH_3)_m$—$(OCR^3HCH_2)_n$—$(O)_o$—, wherein $R^3$ is H or $CH_3$ and m is 0 or a number from 1 to 6, n is a number from 1 to 10, preferably 1 to 6, and o is 0 or 1,
—$(CR^4HCH_2)_p$—, wherein $R^4$ is H or $CH_3$, p is a number from 1 to 10, preferably 1 to 6,
$(CH_3)_q$—$(OCR^5HCH_2)_r$—$(O)_s$—$(CH_3)_t$—, wherein $R^5$ is H or $CH_3$ and q is 0 or a number from 1 to 6, r is a number from 1 to 10, preferably 1 to 6, and s is 0 or 1, and t is a number from 1 to 6, $R^2$ is a group of the formula (II)

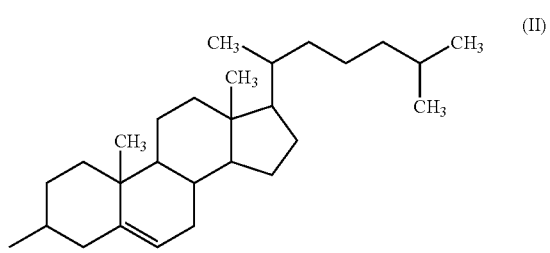

(II)

or a fatty alkyl group or a fatty acid group having 8 to 22 carbon atoms, as well as their physiologically compatible derivatives, in particular salts and trimethyl silyl derivatives.

The compounds according to the invention are suitable in particular for preparing liposomal preparations and for preparing medicaments that can be used for the treatment of animals and humans.

The bisphosphonic acid compounds according to the invention can be present in the form of their acid or also in the form of their salts or trimethyl silyl derivatives. In the trimethyl silyl derivatives at least one of the OH-groups on P is replaced by a trimethyl silyl group. As salts all physiologically compatible salts can be used, in particular, alkaline, alkaline earth, and ammonium salts.

Especially preferred are compounds of the formula (I) in which $R^1$ is OH and $R^2$ is a group of the general formula (II) (i.e., cholesteryl-3-hydroxy-bisphosphonic acid) their soluble salts, with or without spacer molecule. When the group $R^2$ is a fatty alkyl group, the fatty alky group is preferably selected from fatty alkyl groups having 12 to 18 carbon atoms, such as a group derived from dodecyl carboxylic acid or palmitic acid, i.e., the compounds of the formula I are dodecyl bisphosphonic acid or palmitic bisphosphonic acid.

The compounds according to the invention are characterized by a variety of applications, for example, as chelating agents for divalent and trivalent metal ions in technical and industrial applications, as corrosion protection agents in technical and industrial applications, as pharmaceutical active ingredients, as aids for active ingredient transport or as diagnostic agents.

The pharmaceutical/pharmacologically active substances can be selected from any active ingredient such as therapeutic cancer agents, virustatic agents, antibiotics, antimycotic agents, anti-inflammatory agents, bone tissue-stimulating agents or bone tissue-suppressing substances; this list is not all encompassing. Antibiotics can be in particular aminoglycosides, penicillines, cephalosporines, tetracyclines, makrolide, lincosamides, fluoroquinolones, streptogramines, nitroimidazoles, azoles, polyenes, polypeptide antibiotics, antibiotic oligonukleotides, especially gentamycine, amikacine ortobramycine, nafcilline or piperacilline, cefepime or cefuroxime, tetracycline or doxycycline, erythromycine, clarithromycine or azithromycine, clindamycine, ciprofloxacine or moxifloxacine, dalfopristine or quinupristine, metronidazole, miconazole or ketoconazole, amphotericine B, vancomycine or bacitracine. As examples of therapeutic cancer agents folic acid antagonists, alkylating agents, antimetabolites, purine antagonists, pyrimidine antagonists, plant-derived alkaloides, anthracyclines, hormone antagonists, aromatase inhibitors, bisphosphonates or antisense oligonucleotides should be be mentioned.

Further groups of pharmaceutically active substances can be selected from sulfamethoxazole or sulfadiazine, cisplatinum or procarbazine, methotrexat, mercaptopurine, fluorouracil oder cytarabine, vinblastine, vincristine, etoposide or paclitaxel, doxorubicin, epirubicine, pirarubicine, or daunorubicine, gosereline or aminoglutethimide, etidronate, pamidronate, risedronate oder clodronate.

In a further embodiment, the bisphosphonic acids according to the invention are used in the presence of so-called duplex molecules, for example, those that are comprised of covalently bonded fluorouracil and cytosine arabinosides.

The compounds according to the invention are characterized by an affinity to bone and are suitable therefore as aids for the active ingredient transport as well as for transport of diagnostic agents—in these embodiments the compounds according to the invention are bonded to an active agent (active ingredient) and/or a diagnostic agent or are used as carrier materials for these substances. Examples for therapeutic active ingredients are, for example, therapeutic bone cancer agents that are used in bone tissue and in bone marrow of humans and animals.

In another embodiment, the inventive compounds and their derivatives are used as transport molecules for divalent cations, in particular as homing ligands of calcium ions for the treatment of calcium metabolism diseases.

Another embodiment of the present invention concerns theuse of the bisphosphonic acids and their derivatives according to the invention for the treatment of bone metastases.

In the pharmaceutical application, the inventive compounds are preferably used in combination with a conventional carrier material and optionally additional additives.

Another object of the present invention is a method for preparing the compounds of the formula I in which method a compound of the formula III, $R^2$—X—COOH or a reactive derivative thereof, is reacted in a manner known in the art with bisphosphonic acid or tris(trimethylsilyl) phosphite and the obtained products are isolated directly or converted by hydrolysis into the phosphonic acids. The further reaction to the physiologically compatible salts can be realized by reaction with suitable bases.

According to another embodiment of the present invention, the compounds according to the present invention of the formula I are used in a composition in the presence of suitable conjugates. The conjugates can be selected from liposomes, nanoparticles, nanospheres, nanocapsules, micelles, or polymer systems. Preferably, the compounds of the general formula (I) or their derivatives in combination with a mixture of phospholipids, including a uronic acid derivative as an enveloping material or any other enveloping material, can be used wherein the quantity, type and concentration of individual components is arbitrary and selected as a function of the application purpose. As uronic acid derivatives, for example, palmityl-D-glucuronide or galactosyl-D-glucuronide in concentrations of 0.1 mol % to 25 mol % can be used. In one embodiment the bisphosphonic acid derivative according to the invention is bonded to a long-circulating liposome that is modified with a uronic acid derivative as an enveloping substance.

As phospholipids the combination can comprise phosphatidyl choline, phosphatidyl glycerol, phosphatidyl ethanolamine, phosphatidyl inositol, phosphatidyl acid, sphingomyelin, ceramide in their natural, semi-synthetic or synthetic forms as well as stearyl amine and cholesterol, wherein a phospholipid mixture that contains dipalmitoyl phosphatidyl choline and dimyristoyl phosphatidyl glycerol is especially preferred. As polymers, the composition can contain polyvinyl pyrrolidones or polyethylene oxides.

This composition can also contain one or several of the above described active substances in any suitable concentration. These substances can be selective from the pharmaceutically active substances and diagnostic agents already described supra but also from disinfection agents, chemicals, and magnetic particles.

A further object of the present invention concerns a method for producing a liposomal composition wherein a raw mixture of the individual components such as palmityl-D-glucuronide, phospholipids, bisphosphonic acid(s), or a derivative thereof of the general formula (I) and any individual active substance or combinations of active substances can be mixed with one another by ultrasound, high-pressure extrusion or high-pressure homogenization. A liposome product is obtained that preferably has an average particle diameter of 30 to 1,000 nm.

The liposome composition according to the invention is preferably in an aqueous dispersion or lyophilisate. These compositions are particularly suitable for preparing pharmaceutical formulations for injection or inhalation. These formulations contain conventionally one or several active substances. As an example, the aforementioned therapeutic cancer agents, antibiotics, or antisense oligonucleotides can be named.

A further object of the present invention concerns the use of the compounds according to the invention of the formula I for preparing medicaments for treatment of human and animal diseases. The administration of these compounds can be realized intravenously or orally or in any other suitable way.

DESCRIPTION OF PREFERRED EMBODIMENTS

EXAMPLE 1

Preparation of cholesteryl-3-hydroxy-bisphosphonic acid

Cholesteryl chloride was reacted via the corresponding Grignard compound to the carboxylic acid (yield: 35%). This product is then converted in the presence of oxalyl chloride into the acid chloride (yield: 95%)

6.5 g (0.015 mol) acid chloride is dissolved in 150 ml THF. In a nitrogen atmosphere slowly 13.4 g (0.045 mol) O(OSiMe$_3$)$_3$ was added at 0° C. The mixture is stirred at room temperature for three hours.

Subsequently, 0.5 ml (0.03 mol) water is added and the volatile components are removed in vacuum at 90° C.

The solid is dissolved in ethyl acetate and heated for one hour at reflux. Subsequently, filtration is carried out and the remaining solid is washed twice with hexane. The product was dried in vacuum (0.001 torr) (yield: 81%). Cholesteryl-3-hydroxy-bisphosphonic acid: MS molecule ion m/z 561 [M+H]$^+$; $^{31}$P-NMR 21.6 ppm.

EXAMPLE 2

Empty Liposomes Comprised of Dodecyl Bisphosphonic Acid

Liposomes containing soy phosphatidyl choline, cholesterol, palmityl-D-glucuronide and dodecyl bisphosphonic acid in a molar ratio of 1.0:0.3:0.1:0.1 (100 mg/ml) were produced by means of ultrasound. The particle diameter was 120±40 nm. It was determined by photon correlation spectroscopy (light scattering).

EXAMPLE 3

Empty Liposomes Comprised of Palmityl Bisphosphonic Acid

Liposomes containing soy phosphatidyl choline, phosphatidyl glycerol, palmityl-D-glucuronide and palmityl bisphosphonic acid in a molar ratio of 1.0:0.2:0.1:0.1 (100 mg/ml) were produced by means of ultrasound. The particle diameter was 120±40 nm. It was determined by photon correlation spectroscopy (light scattering).

EXAMPLE 4

Empty Liposomes Comprised of cholesteryl-3-hydroxy-bisphosphonic acid

Liposomes containing soy phosphatidyl choline, cholesterol, palmityl-D-glucuronide and cholesteryl-3-hydroxy-bisphosphonic acid in a molar ratio of 0.5:0.14:0.05:0.03 (50 mg/ml) were prepared by means of ultrasound and high-pressure filtration. The particle diameter was 120±40 nm. It was determined by photon correlation spectroscopy (light scattering).

EXAMPLE 5

Cholesteryl Bisphosphonic Acids with Oxyethylene Components as "Spacer" Between Steroid and Acid Group All employed solvents were dried thoroughly, the diols (ethylene glycol, triethylene glycol) were distilled from calcium hydride, and the reactions were carried out in an atmosphere of dry nitrogen.

1. Cholesteryl toluene-p-sulfonate

To a solution of 30 g (77.6 mmol) cholesterol in 250 mm pyridine, 22.2 g (116.4 mmol) of toluene-p-sulfonyl chloride were added. The reaction mixture was stirred for 24 hours at room temperature; subsequently, 200 mm ice water were added slowly. The yellow precipitate was filtered, washed with ethanol (3×70 ml). The product was a white powder in 95% yield (39.9 g).

2. Cholesteryl-hydroxyethylether

A solution of 1 mmol cholesteryl toluene-p-sulfonate and 200 mmol of ethylene glycol or triethylene glycol in dioxane were heated to reflux for 2.5 hours. After removing the solvent in vacuum, the remaining oil was taken up in diethylether and washed with water. The organic phase was dried with magnesium sulfate, filtered and, the solvent removed in vacuum. In the case of cholesteryl hydroxyethylether the solid residue was washed with hexane. A white powder in 86% yield was obtained. In the case of cholesteryl-3,6-dioxaoctane-1-ol a purification on silica gel was required. Yellow impurities were washed out with hexane. The product was washed off with a (90/10) dichloromethane-methanol mixture and solvent was removed in vacuum. The residue was the desired product in a 74% yield.

3. Cholesteryl Oxyethylene Carboxylic Acids 1.1 mmol of nBu Li (1.4 M solution in hexane) was added to a solution of cholesterol and hydroxyethylether (see under 2) in THF at −78° C., the reaction mixture was stirred for 10 minutes and a twofold excess of lithium bromoacetate was added. After 20 minutes the solution was heated to room temperature. After 16 hours at room temperature the mixture was maintained for three hours at 60° C. The solvent was removed in vacuum, diethylether was added, and the organic phase was washed several times with water and dried in vacuum. 2-(cholesteryloxy) acetic acid was isolated in 85% yield; [2-(cholesteryloxy)ethoxy]acetic acid in 60% yield after recrystallization from hexane; {2-[(cholesteryl-3,6-dioxaoctane-1-ol)oxy]ethoxy}acetic acid was isolated in 70% yield in that the solution of the raw product in an ether/pentane mixture (1/1) was passed through a silica gel column and then washed off with a dichloromethane/methanol mixture (5/1).

4. Synthesis of the Corresponding Bisphosphonic Acids

The carboxylic acids from 3 were converted in dichloromethane by means of oxalyl chloride into the acid chlorides that were then reacted without further purification with tris (trimethylsilyl) phosphite in ether, followed by acidic hydrolysis of the obtained trimethylsilylated bisphosphonic acid ester leading to the desired free bisphosphonic acids in 80-95% yield.

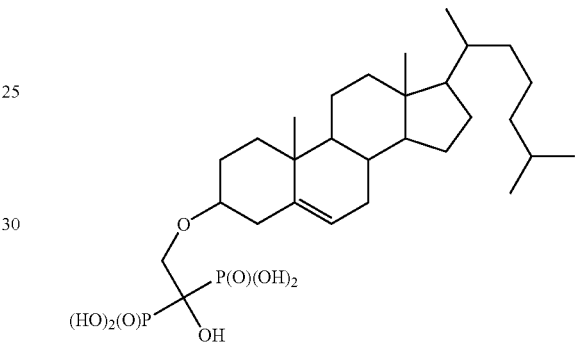

from 2-(cholesteryloxy) acetic acid 2-(2,3,4,7,8,9,10,11,12,13,14,15,16,17-tetradecahydro-10,13-dimethyl-17-(6-methylheptane-2-yl)-1H-cyclopenta[a]phenanthrene-3-yloxy)-1-hydroxy-1-phosphono)ethylphosphonic acid; $C_{29}H_{52}O_8P_2$ (590.31); NMR: $^1H$ (DMSO-$d_6$): 0.3-2.7 ppm (m, 43H), 3.3 ppm (1H), 4.2 ppm (m, 2H), 5.4 ppm (broad, 1H), 10.2 ppm (broad, 5H); $^{31}P$ (DMSO-$d_6$): 18.8 ppm (t, J=11.99 Hz).

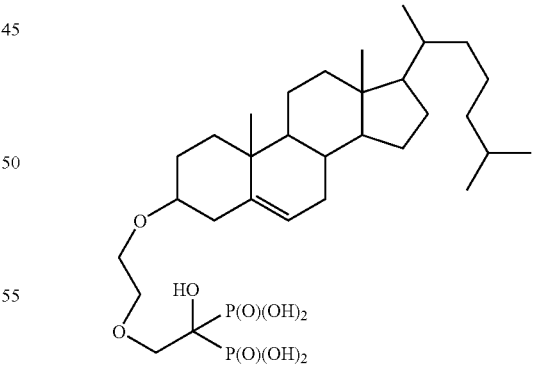

from [2-(cholesteryloxy)ethoxy]acetic acid 2-(2-(2,3,4,7,8,9,10,11,12,13,14,15,16,17-tetradecahydro-10,13-dimethyl-17-(6-methylheptane-2-yl)-1H-cyclopenta[a]phenanthrene-3-yloxy)ethoxy)-1-hydroxy-1-phosphono)ethylphosphonic acid; $C_{31}H_{56}O_9P_2$ (634.3); NMR: $^1H$ (DMSO-$d_6$): 0.59-2.53 ppm (m, 43H), 3.28 ppm (m, 1H), 3.72 ppm (m, 4H), 4.17 ppm (m, 2H), 5.37 ppm (m, 1H), 10.4 ppm (broad, 5H); $^{31}P$ (DMSO-$d_6$): 20.1 ppm (t, J=13.87 Hz).

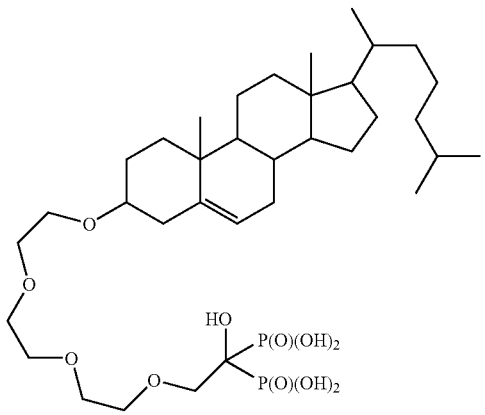

from {2-[(cholesteryl-3,6-dioxaoctane-1-ol)oxy]ethoxy}acetic acid 2-(2-(2-(2-(2,3,4,7,8,9,10,11,12,13,14,15,16,17-tetradecahydro-10,13-dimethyl-17-(6-methyl-heptane-2-yl)-1H-cyclopenta[a]phenanthrene-3-yloxy)ethoxy)ethoxy)ethoxy)-1-hydroxy-1-phosphono)ethylphosphonic acid; $C_{35}H_{64}O_{11}P_2$ (722.39); NMR: $^1H$ (DMSO-$d_6$): 0.20-2.39 ppm (m, 43H), 3.3 ppm (m, 1H), 3.49 ppm (m, 12H), 5.28 ppm (broad, 1H), 3.82 ppm (t, 2H, J=10.99 Hz), 10.8 ppm (broad, 5H); $^{31}P$ (DMSO-$d_6$) 18.8 ppm (t, J=10.9 Hz).

What is claimed is:

1. A bisphosphonic acid of the general formula (I)

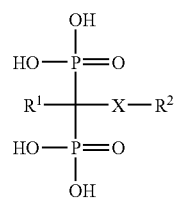

(I)

wherein $R^1$ is H, OH, $C_1$-$C_6$ alkyl $C_1$-$C_6$ alkoxy, $C_1$-$C_6$ hydroxyalkyl, $C_1$-$C_6$ aminoalkyl, $C_1$-$C_6$ halogen alkyl, X is a direct bond, alkylen group with 1 to 20 carbon atoms, $(CH_2)_m$—$(OCR^3HCH_2)_n$—$(O)_o$—, wherein $R^3$ is H or $CH_3$ and m is 0 or a number from 1 to 6, n is a number from 1 to 10, and o is 0 or 1, —$(CR^4HCH_2O)_p$—, wherein $R^4$ is H or $CH_3$, p is a number from 1 to 10, $(CH_2)_q$—$(OCR^5HCH_2)_r$—$(O)_s$—$(CH_3)_t$—, wherein $R^5$ is H or $CH_3$ and q is 0 or a number from 1 to 6, r is a number from 1 to 10, and s is 0 or 1, and t is a number from 1 to 6, $R^2$ is a group of the formula (II)

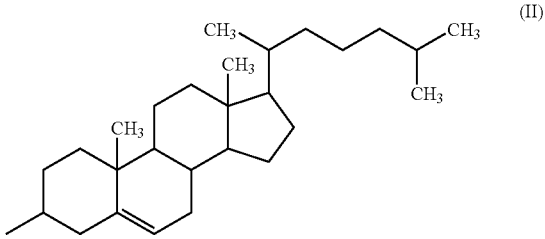

(II)

as well as its physiologically compatible salts and trimethyl silyl compounds.

2. The bisphosphonic acid according to claim 1, wherein $R^1$ is OH.

3. The bisphosphonic acid according to claim 1 as a chelating agent or transport agent for divalent and trivalent metal ions in technical and industrial applications, as a corrosion protection agent in technical and industrial applications, as a pharmaceutical agent, as an additive for active agent transport or as a diagnostic agent.

4. The bisphosphonic acid according to claim 3, wherein the compound of the general formula (I) is bonded to an active agent or a diagnostic agent.

5. The bisphosphonic acid according to claim 4, wherein the active agent or the diagnostic agent is selected from therapeutic cancer agents, virustatic agents, antibiotics, antimycotic agents, anti-inflammatory agents, substances that stimulate bone tissue or suppress bone tissue.

6. A method for preparing the compound of the formula I,

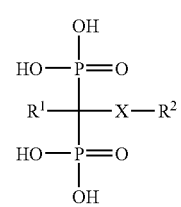

(I)

wherein $R^1$ is H, OH, $C_1$-$C_6$ alkyl, $C_1$-$C_6$ alkoxy, $C_1$-$C_6$ hydroxyalkyl, $C_1$-$C_6$ aminoalkyl, $C_1$-$C_6$ halogen alkyl, X is a direct bond, alkylen group with 1 to 20 carbon atoms, $(CH_2)_m$—$(OCR^3HCH_2)_n$—$(O)_o$—, wherein $R^3$ is H or $CH_3$ and m is 0 or a number from 1 to 6, n is a number from 1 to 10, and o is 0 or 1, —$(CR^4HCH_2O)_p$—, wherein $R^4$ is H or $CH_3$, p is a number from 1 to 10, $(CH_2)_q$—$(OCR^5HCH_2)_r$—$(O)_s$—$(CH_3)_t$—, wherein $R^5$ is H or $CH_3$ and q is 0 or a number from 1 to 6, r is a number from 1 to 10, and s is 0 or 1, and t is a number from 1 to 6, $R^2$ is a group of the formula (II)

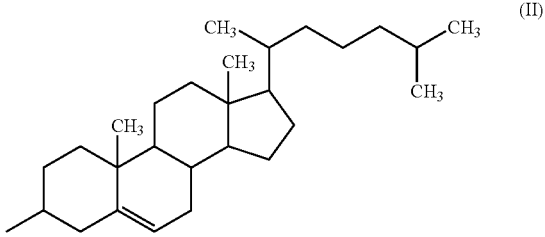

(II)

comprising the steps of reacting a compound $R^2$—X—COOH or an acid chloride thereof in a way known in the art with the bisphosphonic acid or tris(trimethylsilyl) phosphite and isolating the obtained product or converting the obtained product by hydrolysis into the free phosphonic acid.

7. A liposomal composition comprising a compound of the general formula I

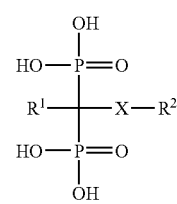

(I)

wherein $R^1$ is H, OH, $C_1$-$C_6$ alkyl, $C_1$-$C_6$ alkoxy, $C_1$-$C_6$ hydroxyalkyl, $C_1$-$C_6$ aminoalkyl, $C_1$-$C_6$ halogen alkyl, X is a direct bond, alkylen group with 1 to 20 carbon atoms, $(CH_2)_m$—$(OCR^3HCH_2)_n$—$(O)_o$—, wherein $R^3$ is H or $CH_3$ and m is 0 or a number from 1 to 6, n is a number from 1 to 10, and o is 0 or 1,
—$(CR^4HCH_2O)_p$—, wherein $R^4$ is H or $CH_3$, p is a number from 1 to 10, $(CH_2)_q$—$(OCR^5HCH_2)_r$—$(O)_s$—$(CH_3)_t$—, wherein $R^5$ is H or $CH_3$ and q is 0 or a number from 1 to 6, r is a number from 1 to 10, and s is 0 or 1, and t is a number from 1 to 6,
$R^2$ is a group of the formula (II)

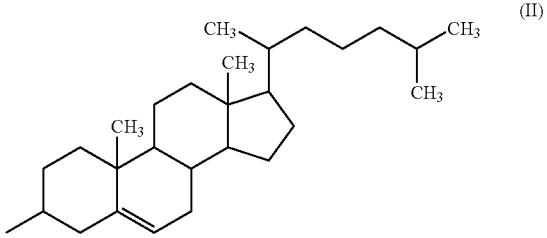

and at least one phospholipid and a uronic acid derivative selected from the group consisting of palmityl-D-glucuronide; galactosyl-D-glucuronide; palmityl-D-glucuronide; and galactosyl-D-glucuronide.

8. The composition according to claim 7, wherein the uronic acid derivative is contained in concentrations of 0.1 mol % to 25 mol %.

9. The composition according to claim 7, wherein the phospholipids are selected from phosphatidyl choline, phosphatidyl glycerol, phosphatidyl ethanolamine, phosphatidyl inositol, phosphatidyl acid, and wherein the composition further comprises lipids selected from sphingomyelin, ceramide as well as stearyl amine and cholesterol.

10. The composition according to claim 7 in the form of an aqueous dispersion or as a lyophylisate.

11. A method for producing a composition according to claim 7, comprising the step of mixing by ultrasound, high-pressure extrusion, or high-pressure homogenization a raw mixture comprising the compound of the general formula I and at least one phospholipid and a uronic acid derivative selected from the group consisting of palmityl-D-glucuronide; galactosyl-D-glucuronide; palmityl-D-glucuronide; and galactosyl-D-glucuronide.

12. The method according to claim 11, wherein the raw mixture contains palmityl-D-glucuronide; phospholipids; bisphosphonic acid(s) of the general formula (I) or a salt thereof; and further contains an individual active agent or a combination of active agents.

13. The composition according to claim 7 comprising palmityl-D-glucuronide; phospholipids; bisphosphonic acid(s) of the general formula (I) or a salt thereof; and any individual active agent or combination of active agents, wherein the active agent is selected from the group consisting of therapeutic cancer agents, virustatic agents, antibiotics, antimycotic agents, anti-inflammatory agents, substances that stimulate bone tissue or suppress bone tissue.

* * * * *